US012636324B2

(12) United States Patent
Lin et al.

(10) Patent No.:    US 12,636,324 B2
(45) Date of Patent:    May 26, 2026

(54) METHOD OF PROMOTING FIRMNESS, ELASTICITY AND WOUND HEALING ABILITY OF THE VULVA AND THE VAGINA

(71) Applicant: NUTRAREX BIOTECH CO., LTD., Taichung City (TW)

(72) Inventors: Meei-Yn Lin, Taichung City (TW); Pin-Chao Huang, Taichung City (TW); Jyun-Ting Syu, Taichung City (TW); Chin-Hsiu Yu, Taichung City (TW); Shao-Yu Lee, Taichung City (TW)

(73) Assignee: NUTRAREX BIOTECH CO., LTD., Taichung City (TW)

( * ) Notice: Subject to any disclaimer, the term of this patent is extended or adjusted under 35 U.S.C. 154(b) by 224 days.

(21) Appl. No.: 18/602,073

(22) Filed: Mar. 12, 2024

(65) Prior Publication Data

US 2025/0288626 A1    Sep. 18, 2025

(51) Int. Cl.
*A61K 35/744*        (2015.01)
*A61K 35/00*         (2006.01)

(52) U.S. Cl.
CPC ...... *A61K 35/744* (2013.01); *A61K 2035/115* (2013.01)

(58) Field of Classification Search
CPC .............................. A61K 35/744; A61P 15/00
See application file for complete search history.

(56) References Cited

U.S. PATENT DOCUMENTS

2016/0375053 A1* 12/2016 Choi .................... A61K 9/0036
424/680

OTHER PUBLICATIONS

Ghailan, Alyaa Zaidan, and Alaa Kareem Niamah. "*Streptococcus thermophilus*: Metabolic Properties, Functional Features, and Useful Applications." Applied Microbiology 5.4 (2025): 101. (Year: 2025).*

* cited by examiner

*Primary Examiner* — Robert J Yamasaki
(74) *Attorney, Agent, or Firm* — WPAT, PC

(57)        ABSTRACT

Provided is a method of promoting firmness, elasticity and wound healing ability of the vulva and the vagina, and the method comprising administering to a subject in need an effective amount of *Streptococcus thermophilus* iHA318 strain and/or its metabolites; wherein, the *Streptococcus thermophilus* iHA318 strain was deposited at German Collection of Microorganisms and Cell Cultures (Deutsche Sammlung von Mikroorganismen und Zellkulturen GmbH, DSMZ) under the accession number DSM 33978. The specific *Streptococcus thermophilus* iHA318 strain and/or its metabolites can exert the beneficial effects of promoting firmness, elasticity and wound healing ability of the vulva and the vagina, such that the problems of the subject can be improved or solved appropriately.

14 Claims, 4 Drawing Sheets

METHOD OF PROMOTING FIRMNESS, ELASTICITY AND WOUND HEALING ABILITY OF THE VULVA AND THE VAGINA

BACKGROUND OF THE INVENTION

1. Field of the Invention

The instant disclosure relates to a method which benefits to the vulva and the vagina, particularly to a method of promoting firmness, elasticity and wound healing ability of the vulva and the vagina.

2. Description of the Prior Arts

The vagina is an elastic, muscular tube with a flexible and soft lining, and the vulva refers to the outside body area around the opening of the vagina. Both the vagina and the vulva are indispensable for human reproduction. The part exposed to the ambient environment of the vagina and the vulva mainly consists of stratified squamous epithelial cells, which provide protection from pathogens and give suitable endurance for friction. Maintaining the firmness and elasticity of stratified squamous epithelial cells is important for the vagina and the vulva to play their innate roles normally. Also, when encountering damages, the wound healing ability of stratified squamous epithelial cells is vital for the vagina and the vulva to reduce the risk of infection and inflammation.

Zonula occludens-1 (ZO-1), also known as tight junction protein-1, is a 220 kDa peripheral membrane protein. ZO-1 is considered to involve in signal transduction at cell-cell junctions and may serve an important role in maintaining tight junction integrity of epithelial cells. It is generally recognized that the expression of ZO-1 positively relates to the tightness of cell-cell junctions, which leads to higher firmness epithelial cells when having higher expression of ZO-1.

Aquaporin-3 (AQP-3) is a protein responsible for regulating water permeability and is expressed in various tissues including the skin, respiratory tract and kidneys, etc. Normally, AQP-3 is located at cell membrane as a membrane water channel and plays a role on controlling in-and-out of water of cells. It is believed that as the expression of AQP-3 in epithelial cells is promoted, the chance of water flowing into epithelial cells increases, thereby hydrating the epithelial cells to obtain higher elasticity and show brighter appearance. Besides, cluster of differentiation 44 (CD44) is a cell surface glycoprotein and participates in a wide variety of cellular functions. One of the known functions of CD44 is a receptor for hyaluronic acid (HA). Since HA has already been used for keeping moisturization and elasticity of the epithelial cells, it is believed that the elevated expression of CD44 in the epithelial cells also leads to higher elasticity and moisturization.

The vaginal relaxation syndrome basically indicates a condition of laxity of the vagina and the vulva because of tissue relaxation. Main causes of the vaginal relaxation syndrome are vaginal childbirth or aging. Problems such as loss of sensation, decreased sexual satisfaction, and decreased self-confidence, etc. due to the vaginal relaxation syndrome may seriously bother the normal life of women. The effective option for treating the vaginal relaxation syndrome may be surgical approaches, but surgical approaches have a risk of remaining scar and are not very receptive as an invasive procedure in a sensitive area.

Accordingly, there is still a need to research and develop a method that can promote firmness, elasticity and wound healing ability of the vulva and the vagina, thereby providing a female human in need with a more receptive option.

SUMMARY OF THE INVENTION

In view of the problems in the prior art, an objective of the present invention is to provide a more receptive option for improving looseness symptoms at the vagina and/or the vulva, including the vaginal relaxation syndrome, by promoting firmness, elasticity and wound healing ability of the vulva and the vagina.

To achieve the foresaid objectives, the present invention provides a method of promoting firmness, elasticity and wound healing ability of the vulva and the vagina, and the method comprising administering to a subject in need an effective amount of *Streptococcus thermophilus* iHA318 strain and/or its metabolites; wherein, the *Streptococcus thermophilus* iHA318 strain was deposited at German Collection of Microorganisms and Cell Cultures (Deutsche Sammlung von Mikroorganismen und Zellkulturen GmbH, DSMZ) under the accession number DSM 33978.

By adopting the specific *Streptococcus thermophilus* iHA318 strain and/or its metabolites, and administering to the subject in need, such as female human suffering from the vaginal relaxation syndrome, the properties of firmness, elasticity and wound healing ability of the vulva and the vagina can be promoted, such that the problems of the subject can be improved or solved appropriately.

In accordance with the present invention, the said "*Streptococcus thermophilus* iHA318 strain" comprises viable bacteria, inactive bacteria or a combination thereof. The said inactive bacteria may be obtained by sterilizing with an autoclave at 121° C. for 15 minutes.

In some embodiments of the present invention, the foresaid *Streptococcus thermophilus* iHA318 strain and/or its metabolites may promote the expression of ZO-1, AQP-3, CD44 or any combination thereof in the stratified squamous epithelial cells of the vulva and the vagina.

In some embodiments of the present invention, the foresaid *Streptococcus thermophilus* iHA318 strain and/or its metabolites may promote the migration ability of the stratified squamous epithelial cells of the vulva and the vagina.

In some embodiments of the present invention, the vulva and the vagina may comprise the stratified squamous epithelial cells of the vulva and the vagina.

In some embodiments of the present invention, the promoted properties of the vulva and the vagina may indicate the promoted properties of the stratified squamous epithelial cells of the vulva and the vagina.

In some embodiments of the present invention, the foresaid metabolites of *Streptococcus thermophilus* iHA318 strain may be generated by cultivating under an environment suitable for its growth. For example, the foresaid *Streptococcus thermophilus* iHA318 strain may be, but is not limited to, cultivated in De Man-Rogosa-Sharpe (MRS) medium or M17 medium for about 16 to 24 hours, and then the medium after culturing containing the metabolites of *Streptococcus thermophilus* iHA318 strain (also named as a conditioned medium) could be obtained. Optionally, the solids, including bacteria, in the conditioned medium containing the metabolites could be further filtered and removed.

In some embodiments of the present invention, the foresaid conditioned medium may be dried or lyophilized to be a powder. Optionally, the foresaid conditioned medium may mix with, but is not limited to, a carrier, an excipient, a filler, a stabilizer, a cryoprotectant or any combination thereof in advance to obtain a mixture, and then the mixture is dried or lyophilized to be a powder.

In some embodiments of the present invention, the foresaid *Streptococcus thermophilus* iHA318 strain and/or its metabolites may be dried or lyophilized to be powders. Optionally, the foresaid *Streptococcus thermophilus* iHA318 strain and/or its metabolites may mix with, but is not limited to, a carrier, an excipient, a filler, a stabilizing agent, a cryoprotectant or any combination thereof in advance to obtain a mixture, and then the mixture is dried or lyophilized to be a powder.

In some embodiments of the present invention, the suitable medium for cultivating the foresaid *Streptococcus thermophilus* iHA318 strain may be, but is not limited to, MRS medium containing small molecule nitrogen source, e.g., urea, or M17 medium containing small molecule nitrogen source.

In some embodiments of the present invention, the subject in need may indicate a female human having looseness symptoms at the vagina and/or the vulva. In some embodiments of the present invention, the subject in need may indicate a female human having vaginal relaxation syndrome.

In accordance with the present invention, the effective amount may depend on the actual need without specific limitations as the desired effects of the present invention can be achieved. In some embodiments of the present invention, the effective amount may be $1 \times 10^3$ CFU (as the foresaid *Streptococcus thermophilus* iHA318 strain) per day to $1 \times 10^{10}$ CFU per day.

In accordance with the present invention, the choice of administration manner may depend on the actual need without specific limitations as the desired effects of the present invention can be achieved. For example, the administration manner may be, but is not limited to, oral administration, i.e., through an oral route, or topical administration.

In some embodiments of the present invention, the subject in need is administrated with a medicament, and the medicament comprises the foresaid *Streptococcus thermophilus* iHA318 strain and/or its metabolites and a pharmaceutically acceptable carrier. The foresaid pharmaceutically acceptable carrier may comprise, but is not limited to, a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome or any combination thereof.

In some embodiments of the present invention, the administration manner may be oral administration or topical administration with a medicament comprising the foresaid *Streptococcus thermophilus* iHA318 strain and/or its metabolites and the foresaid pharmaceutically acceptable carrier.

In some embodiments of the present invention, the administration manner may be oral administration with a medicament comprising the foresaid *Streptococcus thermophilus* iHA318 strain and/or its metabolites, and the dosage form of the medicament may be, but is not limited to, a solution, a suspension, a powder, a tablet, a pill, a syrup, a lozenge, a troche, a chewing gum or a capsule.

In some embodiments of the present invention, the administration manner may be topical administration with a medicament comprising the foresaid *Streptococcus thermophilus* iHA318 strain and/or its metabolites, and the dosage form of the medicament may be, but is not limited to, a solution, a suspension, an ointment, a cream or any combination thereof.

Other objectives, advantages and novel features of the instant disclosure will become more apparent from the following detailed description when taken in conjunction with the accompanying drawings.

Figure 1A:
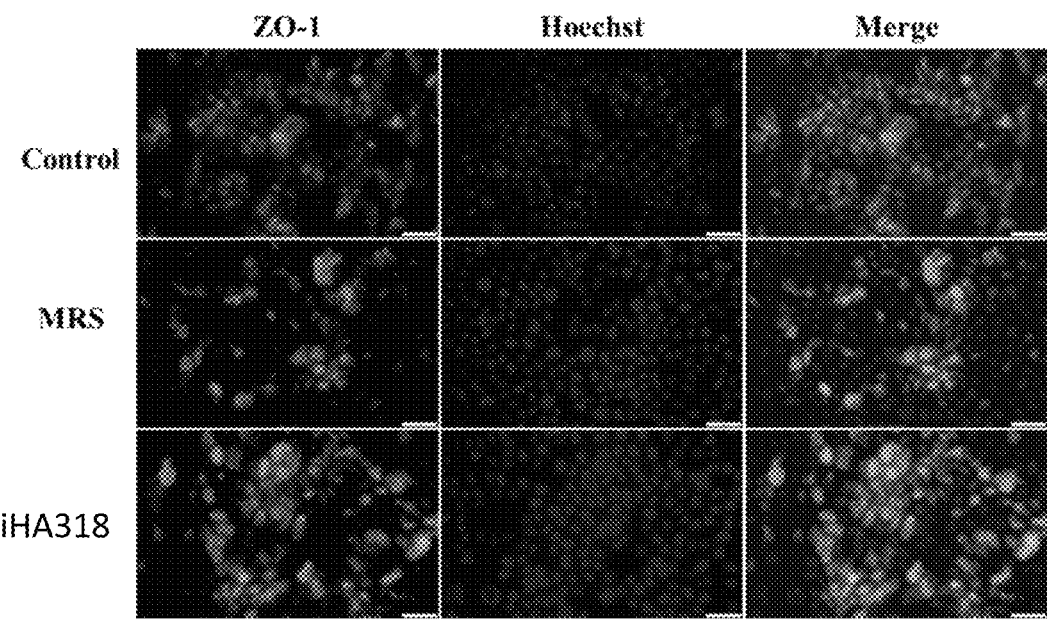
FIG. 1A is result of immunofluorescence staining of ZO-1 in A431 cells with the cell nuclei stained by Hoechst dye, and their merge images of the Control group, the MRS group and the iHA318 group.

DETAILED DESCRIPTION OF THE
PREFERRED EMBODIMENTS

Hereinafter, some embodiments and test examples are exemplified to illustrate the implementation and the effects of the present invention. One person skilled in the art can easily realize the advantages and effects of the present invention in accordance with the contents of the specification. Various modifications and variations could be made in order to practice or apply the present invention without departing from the spirit and scope of the invention.

Preparation Example: *Streptococcus thermophilus*
iHA318 Strain Sample

Frozen *Streptococcus thermophilus* iHA318 strain (hereinafter referred to as iHA318 strain) was thawed and cultured in MRS medium with concentration of 1 vol % under an anaerobic environment at 37° C. for 16 hours to 24 hours, so as to activate the iHA318 strain. Then, 100 μL of the MRS medium with activated iHA318 strain was added to 10 mL of MRS medium and cultured under an anaerobic environment at 37° C. for 16 hours to 24 hours. Afterward, the MRS medium with iHA318 strain was sterilized by using an autoclave at 121° C. for 15 minutes to obtain the iHA318 strain sample for the following experiments.

Test Example 1: Expression of ZO-1 in A431 Cells (1) Immunofluorescence Staining of ZO-1 in A431 Cells 2000 μL of Dulbecco's Modified Eagle Medium (DMEM) containing 10% fetal bovine serum (FBS) and 1% penicillin-streptomycin was added in each well of a six-well plate with a glass slide (length: 21 mm; width: 21 mm) in bottom. Then, A431 cells (purchased from Japanese Collection of Research Bioresources (JCRB); item number: JCRB9009, derived from an epidermal carcinoma of the vulva taken from an 85-year-old female human) were added in the DMEM with a concentration of $1\times10^6$ cells per well, and cultured under conditions of 5% $CO_2$, 37° C. for 24 hours to make the A431 cells attach to the glass slide uniformly.

Afterward, sterilized and double distilled water (sterilized $ddH_2O$), MRS medium and the iHA318 strain sample were respectively added into DMEM containing 5% FBS and 1% penicillin-streptomycin to obtain a sterilized $ddH_2O$ sample, an MRS sample and an iHA318 sample, and the concentration of sterilized $ddH_2O$ was 2 vol %, the concentration of MRS medium was 2 vol % and the concentration of the iHA318 strain sample was 2 vol %. Next, 2 mL of the sterilized $ddH_2O$ sample, the MRS sample and the iHA318 sample were respectively added into the well containing attached A431 cells and then co-cultured at 37° C. for 24 hours. The A431 cells treated with the sterilized $ddH_2O$ sample, the MRS sample and the iHA318 sample were marked as Control group, MRS group and iHA318 group, respectively.

After completion of the co-culture, the glass slides of the Control group, the MRS group and the iHA318 group were taken out and washed with PBS (phosphate buffered saline) twice. Next, 100 μL of BSA (bovine serum albumin) blocking buffer (1% BSA in PBS) was added on each glass slide for 15 minutes, and then the blocking buffer was removed and the glass slides were washed with PBS twice. Next, 4% of paraformaldehyde (PFA) was used to fix the A431 cells on the glass slides for 20 minutes, and then PFA was removed and the glass slides were washed with PBS for three times. Next, 150 μL, 0.2% of Triton X-100 was added on each glass slide for 10 minutes, and then Triton X-100 was removed and the glass slides were washed with PBS for three times. Next, 100 μL of BSA blocking buffer was added on each glass slide for 15 minutes, and then the BSA blocking buffer was removed and the glass slides were washed with PBS twice. Next, 100 μL of diluted rabbit anti-ZO-1 primary antibody (purchased from iReal biotechnology, Inc.; item number: IR56-184) with dilution ratio of 1:100 in BSA blocking buffer was added on each glass slide for 60 minutes, and then the primary antibody was removed and the glass slides were washed with PBS for three times. Next, 100 μL of BSA blocking buffer was added on each glass slide for 15 minutes, and then the BSA blocking buffer was removed and the glass slides were washed with PBS twice. Next, 100 μL of diluted Alexa Fluor 488 anti-rabbit IgG secondary antibody (purchased from Invitrogen; item number: A-11008) with dilution ratio of 1:100 in BSA blocking buffer was added on each glass slide for 30 minutes, and then the secondary antibody was removed and the glass slides were washed with PBS for three times. Next, 100 μL of 0.2 μg/mL Hoechst 33342 dye was used to stain cell nucleus for 30 minutes. Last, the glass slides were mounted, dried and then were placed on fluorescence microscope for photographing.

The exemplary results of immunofluorescence staining for the Control group, the MRS group and the iHA318 group were shown in FIG. 1A. The fluorescence levels of ZO-1 in A431 cells of the iHA318 group were obviously higher than those in the Control group and the MRS group.

(2) Quantification for ZO-1 Fluorescence Intensity

Figure 1B:
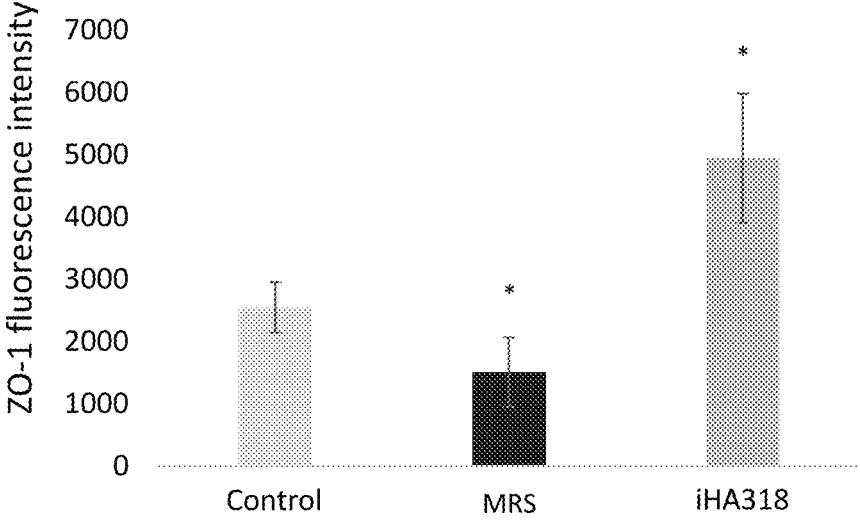
FIG. 1B is quantification result of the ZO-1 fluorescence intensity of the Control group, the MRS group and the iHA318 group based on the result of FIG. 1A.

The results of immunofluorescence staining of ZO-1 in A431 cells for the Control group, the MRS group and the iHA318 group were quantified by ImageJ software for obtaining the ZO-1 fluorescence intensity and shown in FIG. 1B. Briefly, when operating ImageJ software, selected a function of "set measurements" in "analyze menu", and then made sure the models of "area integrated intensity" and "mean gray value" were selected. Then, selected a function of "measure" to obtain total area of cells with fluorescence.

In FIG. 1B, the ZO-1 fluorescence intensity of the iHA318 group was obviously more than the Control group and had statistically significant difference with p-value less than 0.05 after analyzing by t-test.

Accordingly, it was verified that the expression of ZO-1 in A431 cells could actually be elevated after treating with the iHA318 strain sample.

Test Example 2: Expression of AQP-3 and CD44 in A431 Cells

3000 μL of DMEM containing 10% FBS and 1% penicillin-streptomycin was added in each well of a six-cm dish. Then, A431 cells were added in the DMEM with a concentration of $1\times10^6$ cells per well, and cultured under conditions of 5% $CO_2$, 37° C. for 24 hours to make the A431 cells attach to the well bottom uniformly.

Afterward, according to the procedures of Test Example 1, a sterilized $ddH_2O$ sample, an MRS sample and an iHA318 sample were also obtained, and the concentration of sterilized $ddH_2O$ was 1 vol %, the concentration of MRS medium was 1 vol % and the concentration of the iHA318 strain sample was 1 vol %. Next, 6 mL of the sterilized $ddH_2O$ sample, the MRS sample and the iHA318 sample were respectively added into the wells containing attached A431 cells and then co-cultured at 37° C. for 24 hours. The A431 cells treated with the sterilized $ddH_2O$ sample, the MRS sample and the iHA318 sample were marked as Control group, MRS group and iHA318 group, respectively.

Next, the A431 cells of each group were collected and added into 180 μL to 200 μL of lysis buffer, and then lysed by an ultrasonic processor with power of 30% for 15 minutes to obtain whole cell lysates of the Control group, the MRS group and the iHA318 group. Afterward, the total protein amounts in the whole cell lysates of each group were obtained by following the instructions of a DC (detergent compatible) Protein Assay Reagents Package (purchased from Bio-Rad; item number: #5000116).

Next, equal amount of total protein of each group was subjected to SDS-PAGE and western blotting procedures. During the western blotting, primary antibodies for AQP-3 (purchased from Abcam; item number: ab125219; diluted with a ratio of 1:1000 in 1% BSA-PBS buffer), CD44 (purchased from Elabscience; item number: E-AB-11364; diluted with a ratio of 1:1000 in 1% BSA-PBS buffer) and β-actin (purchased from Elabscience; item number: E-AB-48018; diluted with a ratio of 1:5000 in 1% BSA-PBS buffer) were used for specifically binding different targeted proteins at 4° C. for 16 hours, and secondary antibodies purchased from iREAL Biotechnology were used for binding the primary antibodies. After completion of the western blotting, enhanced chemiluminescence detection (ECL) solution was used to make the targeted protein bands, i.e., AQP-3, CD44 and β-actin, show detectable signals. Afterward, the relative signal intensities of protein bands of AQP-3, CD44 and β-actin of the Control group, the MRS group and the iHA318 group were analyzed and quantified by a function "densitometry analysis" of ImageJ software, which could represent the expression of these proteins in A431 cells of all groups. As the expression of β-actin in A431 cells was considered as conservative after different treatments, the signal intensities of AQP-3 and CD44 were both divided by the signal intensity of β-actin, such that the expression of AQP-3 and CD44 could be compared among the Control group, the MRS group and the iHA318 group.

Figure 2:
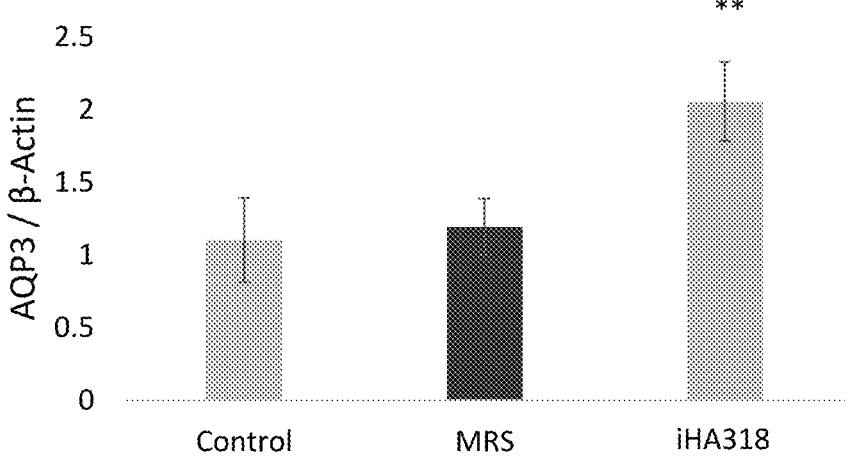
FIG. 2 is quantification result of AQP-3 expression in A431 cells determined by western blotting and comparing to β-actin expression of the Control group, the MRS group and the iHA318 group.

In FIG. 2, the ratios of the signal intensity of AQP-3 to β-actin of the Control group, the MRS group and the iHA318 group were shown. It was clear that the expression of AQP-3 of the iHA318 group was obviously higher than the Control group and had statistically significant difference with p-value less than 0.01 after analyzing by t-test.

Figure 3:
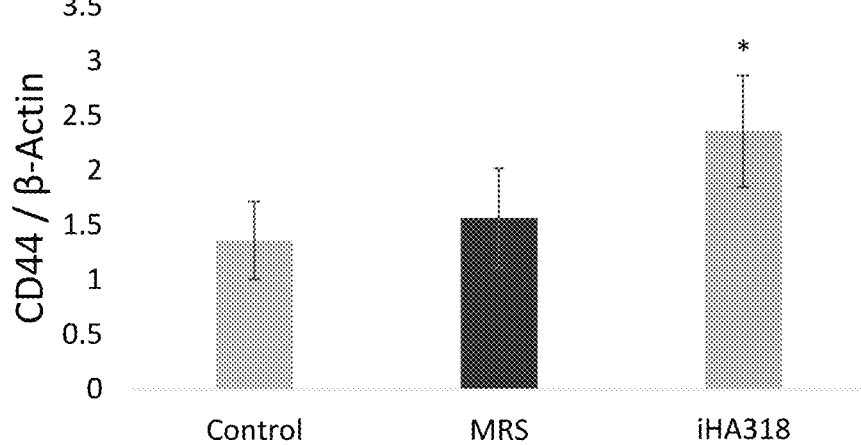
FIG. 3 is quantification result of CD44 expression in A431 cells determined by western blotting and comparing to β-actin expression of the Control group, the MRS group and the iHA318 group.

In FIG. 3, the ratios of the signal intensity of CD44 to β-actin of the Control group, the MRS group and the iHA318 group were shown. It was clear that the expression of CD44 of the iHA318 group was obviously higher than the Control group and had statistically significant difference with p-value less than 0.05 after analyzing by t-test.

Accordingly, it was verified that the expression of AQP-3 and CD44 in A431 cells could actually be elevated after treating with the iHA318 strain sample.

Test Example 3: Evaluation of Wound Healing Ability

The wound healing ability could be evaluated by cell migration ability. The following experiments were to determine the cell migration ability of A431 cells after treating with different samples.

(1) Cells Distribution

100 μL of DMEM containing 10% FBS and 1% penicillin-streptomycin was added in each well of a six-well plate with cell inserts (purchased from IBIDI GmbH; item number: 80209) placed on the bottom of each well. Then, A431 cells were added into the DMEM with a concentration of $2 \times 10^5$ cells per well, and cultured under conditions of 5% $CO_2$, 37° C. for 24 hours to make the A431 cells attach to the well bottom uniformly.

After the cell attached, the cell inserts were removed. Meanwhile, according to the procedures of Test Example 1, a sterilized $ddH_2O$ sample, an MRS sample and an iHA318 sample were also obtained, and the concentration of sterilized $ddH_2O$ was 2 vol %, the concentration of MRS medium was 2 vol % and the concentration of the iHA318 strain sample was 2 vol %. Next, 2 mL of the sterilized $ddH_2O$ sample, the MRS sample and the iHA318 sample were respectively added into the wells containing attached A431 cells and then co-cultured at 37° C. for 24 hours. The A431 cells treated with the sterilized $ddH_2O$ sample, the MRS sample and the iHA318 sample were marked as Control group, MRS group and iHA318 group, respectively.

Figure 4A:
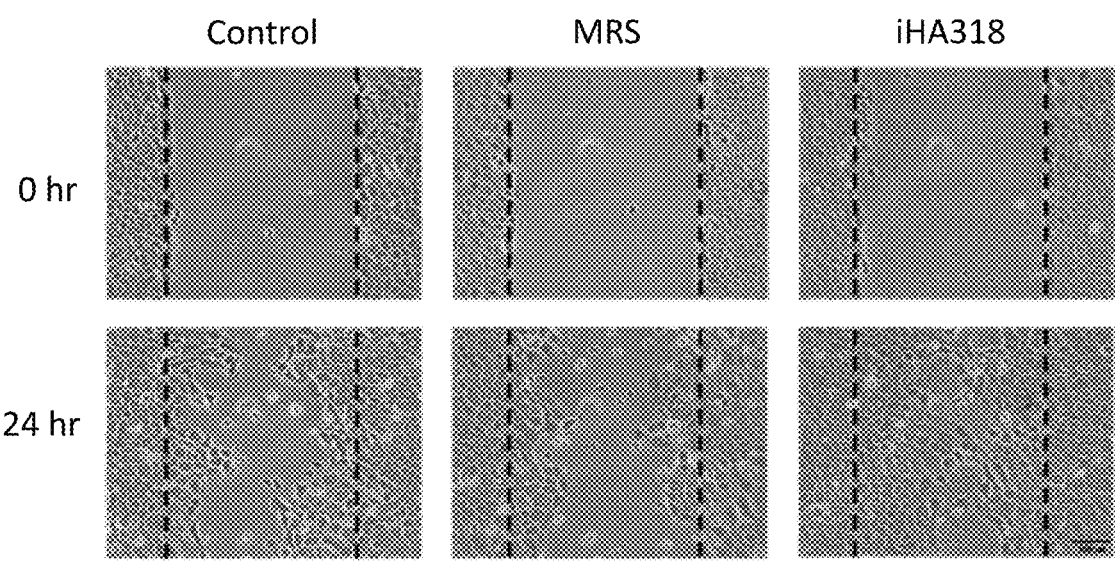
FIG. 4A is result of cell migration ability test, which shows the distribution of A431 cells at 0 hour and at 24 hours of the Control group, the MRS group and the iHA318 group.

During the foresaid sample treatment, after the samples were just added, the cell distributions of the Control group, the MRS group and the iHA318 group were recorded by a camera and the images were marked as 0 hr shown in FIG. 4A. After the samples were added for 24 hours, the cell distributions of the Control group, the MRS group and the iHA318 group were also recorded by the camera and the images were marked as 24 hr shown in FIG. 4A.

In FIG. 4A, at 0 hr, the A431 cells of all three groups located in the left and right sides with nearly no cells on the central path. At 24 hr, the A431 cells of the iHA318 group migrated to the central path and almost fully occupied the central path, while the A431 cells of the Control group and the MRS group migrated to the central path but not fully occupied the central path. Obviously, the cell migration ability of the iHA318 group was higher than the Control group and the MRS group.

(2) Quantification for Cell Migration Ability

The results of cell migration ability of the A431 cells for the Control group, the MRS group and the iHA318 group were quantified by ImageJ software to analyze the areas of the A431 cells located in the central path at 0 hr and 24 hr. Then, the area difference between 0 hr and 24 hr of the Control group was defined as 100%, and the results of the area differences of the MRS group and the iHA318 group were shown in FIG. 4B, which could represent the relative wound healing area.

Figure 4B:
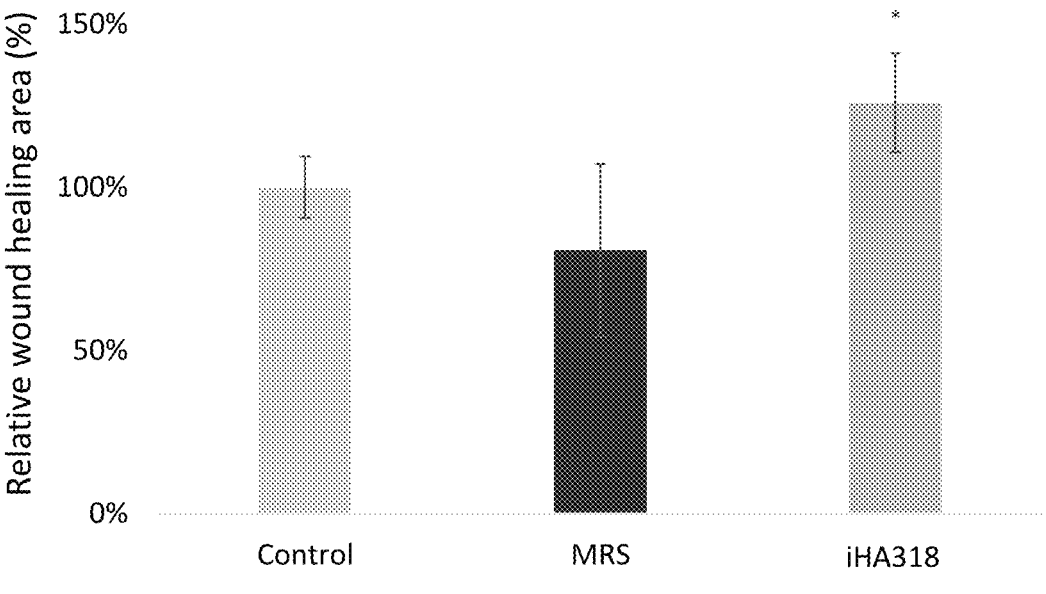
FIG. 4B is quantification result based on the result of FIG. 4A, which represents the relative wound healing area of the Control group, the MRS group and the iHA318 group.

In FIG. 4B, the relative wound healing area of the iHA318 group was obviously more than the Control group and had statistically significant difference with p-value less than 0.05 after analyzing by t-test.

Accordingly, it was verified that the wound healing ability could actually be elevated after treating with the iHA318 strain sample.

Therefore, based on the foresaid Test Examples, the iHA318 strain sample actually elevates the expression of ZO-1, AQP-3 and CD44 in the A431 cells, which may lead to promoted firmness and elasticity of the vulva and the vagina. Meanwhile, the iHA318 strain sample also can enhance the cell migration ability of the A431 cells, which indicate enhanced wound healing ability of the vulva and the vagina.

In summary, as the present invention adopts the specific *Streptococcus thermophilus* iHA318 strain and/or its metabolites, the subject in need, such as female human suffering from the vaginal relaxation syndrome, can obtain the beneficial effects of promoted firmness, elasticity and wound healing ability of the vulva and the vagina, such that the problems of the subject can be improved or solved appropriately, thereby having high developmental potential and value.

Deposit of Biological Material: *Streptococcus thermophilus* iHA318 Strain

Depository Institute: German Collection of Microorganisms and Cell Cultures (Deutsche Sammlung von Mikroorganismen and Zellkulturen GmbH, DSMZ); Address of Depository Institute: Inhoffenstraße 7 B, 38124 Braunschweig, Germany; Date of Deposit: Aug. 17, 2021; Accession number of Deposit: DSM 33978. The *Streptococcus thermophilus* iHA318 strain designated as accession number of DSM 33978 was deposited under the Budapest Treaty by the International Depositary Authority (IDA), i.e., the foresaid German Collection of Microorganisms and Cell Cultures, on Aug. 17, 2021, and will be publicly available upon granting of the referenced application.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method of promoting firmness, elasticity and wound healing ability of the vulva and the vagina, and the method comprising administering to a subject in need an effective amount of *Streptococcus thermophilus* strain and/or its metabolites; wherein, the *Streptococcus thermophilus* strain was deposited at German Collection of Microorganisms and Cell Cultures (Deutsche Sammlung von Mikroorganismen und Zellkulturen GmbH, DSMZ) under the accession number DSM 33978;

wherein promoting wound healing ability of the vulva and the vagina comprises promoting cell migration ability of the stratified squamous epithelial cells of the vulva and the vagina;

wherein the effective amount is $1 \times 10^3$ CFU per day to $1 \times 10^{10}$ CFU per day;

wherein the metabolites of the *Streptococcus thermophilus* strain are generated by cultivating the *Streptococcus thermophilus* strain in MRS medium under an anaerobic environment at 37° C. for 16 to 24 hours.

2. The method as claimed in claim 1, wherein promoting firmness of the vulva and the vagina comprises promoting the expression of ZO-1 in the stratified squamous epithelial cells of the vulva and the vagina.

3. The method as claimed in claim 1, wherein promoting elasticity of the vulva and the vagina comprises promoting the expression of AQP-3 in the stratified squamous epithelial cells of the vulva and the vagina.

4. The method as claimed in claim 1, wherein promoting elasticity of the vulva and the vagina comprises promoting the expression of CD44 in the stratified squamous epithelial cells of the vulva and the vagina.

5. The method as claimed in claim 1, wherein the vulva and the vagina comprise the stratified squamous epithelial cells of the vulva and the vagina.

6. The method as claimed in claim 1, wherein the *Streptococcus thermophilus* strain and/or its metabolites are lyophilized to be powders.

7. The method as claimed in claim 1, wherein a medium for cultivating the *Streptococcus thermophilus* strain comprises MRS medium or M17 medium.

8. The method as claimed in claim 1, wherein a medium for cultivating the *Streptococcus thermophilus* strain is MRS medium containing small molecule nitrogen source.

9. The method as claimed in claim 8, wherein the small molecule nitrogen source is urea.

10. The method as claimed in claim 1, wherein the subject in need comprises a female human having looseness symptoms at the vagina and/or the vulva.

11. The method as claimed in claim 1, wherein the *Streptococcus thermophilus* strain and/or its metabolites are administered to the subject in need by oral administration.

12. The method as claimed in claim 1, wherein the *Streptococcus thermophilus* strain and/or its metabolites are administered to the subject in need by topical administration.

13. The method as claimed in claim 1, wherein the subject in need is administrated with a medicament, and the medicament comprises the *Streptococcus thermophilus* strain and/or its metabolites and a pharmaceutically acceptable carrier.

14. The method as claimed in claim 13, wherein the pharmaceutically acceptable carrier comprises a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome or any combination thereof.

\* \* \* \* \*